(12) United States Patent
Liang et al.

(10) Patent No.: US 11,707,383 B2
(45) Date of Patent: Jul. 25, 2023

(54) INNER DRAINAGE BIOMIMETIC STENT FOR GLAUCOMA AND USE THEREOF

(71) Applicant: Wenzhou Xiaoliang Medical Technology Co., Ltd., Wenzhou (CN)

(72) Inventors: Yuanbo Liang, Wenzhou (CN); Xingyi Li, Wenzhou (CN); Changcan Shi, Wenzhou (CN); Cheng Hu, Wenzhou (CN)

(73) Assignee: SuZhou Purevision Medical Technology Co., LTD., Suzhou (CN)

( * ) Notice: Subject to any disclaimer, the term of this patent is extended or adjusted under 35 U.S.C. 154(b) by 1073 days.

(21) Appl. No.: 16/329,707

(22) PCT Filed: Mar. 31, 2017

(86) PCT No.: PCT/CN2017/078966
§ 371 (c)(1),
(2) Date: Feb. 28, 2019

(87) PCT Pub. No.: WO2017/181836
PCT Pub. Date: Oct. 26, 2017

(65) Prior Publication Data
US 2021/0128355 A1    May 6, 2021

(30) Foreign Application Priority Data
Apr. 21, 2016  (CN) .......................... 201610249470.0

(51) Int. Cl.
*A61F 9/007*     (2006.01)
*A61M 27/00*     (2006.01)

(52) U.S. Cl.
CPC .......... *A61F 9/00781* (2013.01); *A61F 9/007* (2013.01); *A61F 2230/0006* (2013.01); *A61F 2240/001* (2013.01); *A61M 27/002* (2013.01)

(58) Field of Classification Search
CPC .................. A61F 9/00781; A61F 9/007; A61F 2230/0006; A61F 2240/001; A61F 2230/0017; A61M 27/002; A61M 25/0026
See application file for complete search history.

(56) References Cited

U.S. PATENT DOCUMENTS 4,328,803 A * 5/1982 Pape .................... A61F 9/00781
                                                604/28
5,147,284 A * 9/1992 Fedorov .................... A61F 2/14
                                                600/14

(Continued)

FOREIGN PATENT DOCUMENTS

CN    201835535 U    5/2011
CN    103815986 A    5/2014

(Continued)

*Primary Examiner* — Susan S Su
*Assistant Examiner* — Ted Yang
(74) *Attorney, Agent, or Firm* — Yiu F. Au; Au Law Office, P.C.

(57) ABSTRACT

A method for manufacturing an inner drainage biomimetic stent for glaucoma. The inner drainage biomimetic stent for glaucoma comprises: a cylinder tube body with a hollow structure, and a plurality of straight tubes, provided inside the hollow structure of the tube body, for supporting a tube wall of the tube body. Proper placement of the inner drainage biomimetic stent for glaucoma can direct an aqueous humour to smoothly flow through an orifice expanded by the biomimetic stent, into Schlemm's canal. A collapsed Schlemm's canal is re-expanded by the flow of the aqueous humour to direct the aqueous humour to a collector canal, thereby lowering an intraocular pressure and achieving the goal of glaucoma treatment

13 Claims, 4 Drawing Sheets

(56) References Cited

U.S. PATENT DOCUMENTS

| | | | |
|---|---|---|---|
| 2002/0013546 A1 | 1/2002 | Grieshaber et al. | |
| 2003/0055372 A1* | 3/2003 | Lynch | A61F 9/00781 604/8 |
| 2004/0050392 A1* | 3/2004 | Tu | A61F 9/00781 128/898 |
| 2004/0210181 A1* | 10/2004 | Vass | A61F 9/00781 604/8 |
| 2005/0154373 A1 | 7/2005 | Deutsch | |
| 2007/0293807 A1* | 12/2007 | Lynch | A61F 9/00781 604/8 |
| 2007/0293872 A1 | 12/2007 | Peyman | |
| 2011/0144559 A1* | 6/2011 | Lafdi | B82Y 5/00 604/8 |
| 2012/0089073 A1* | 4/2012 | Cunningham, Jr. | A61F 9/00781 604/9 |
| 2012/0302861 A1* | 11/2012 | Marshall | A61F 9/00781 600/398 |
| 2014/0163448 A1* | 6/2014 | Lind | A61F 9/00781 604/9 |
| 2014/0243729 A1* | 8/2014 | Rynerson | A61F 9/00781 604/8 |
| 2014/0276656 A1 | 9/2014 | Bian et al. | |
| 2015/0005893 A1 | 1/2015 | Harrah et al. | |
| 2015/0157504 A1* | 6/2015 | Korigodskiy | A61F 9/00781 604/8 |
| 2015/0257928 A1* | 9/2015 | Iseli | A61F 9/0017 604/521 |
| 2016/0058616 A1* | 3/2016 | Camras | A61F 9/00781 604/9 |

FOREIGN PATENT DOCUMENTS

| | | |
|---|---|---|
| CN | 103932841 A | 7/2014 |
| CN | 105434103 A | 3/2016 |
| CN | 105997341 A | 10/2016 |
| GB | 2558107 A | 7/2018 |
| WO | WO 00/64393 A1 | 11/2000 |
| WO | WO 2009/029744 A1 | 3/2009 |
| WO | WO 2012/142473 A1 | 10/2012 |
| WO | WO 2015/108970 A1 | 7/2015 |

* cited by examiner

INNER DRAINAGE BIOMIMETIC STENT FOR GLAUCOMA AND USE THEREOF

RELATED APPLICATIONS

The present application is a National Phase entry of PCT Application No. PCT/CN2017/078966, filed Mar. 31, 2017, which claims priority to Chinese Patent Application No. 201610249470.0, filed Apr. 21, 2016, the disclosures of which are hereby incorporated by reference herein in their entirety.

FIELD OF THE INVENTION

The present invention relates to the field of medical devices, in particular to a method for preparation of an alternative biomimetic stent for glaucoma internal drainage and a method for using the same.

BACKGROUND

Glaucoma is a disease with damaged optic nerve caused by pathological high intraocular pressure, for which controlling intraocular pressure is a primary treatment approach. Although antiglaucomatous medications and laser technology provide the technology and possibility for controlling intraocular pressure, a considerable number of patients with glaucoma eventually have to undergo surgical treatment due to the particularity of this disease. Currently, the prevalent operating mode for glaucoma is trabeculectomy, but the filtration surgery of glaucoma has many uncertainties and relatively high occurrence of complications such as postoperative ocular hypotension, shallow anterior chamber, choroidal detachment, cystoid macular edema, as well as problems in failure of operation, filtering bleb scarring and the like. It has always been the striving direction of ophthalmologists to seek a safe and reliable surgical method.

Glaucoma surgery has made a leap from full-thickness sclerectomy to trabeculectomy under scleral flap protection as the latter manages to avoid some serious postoperative complications. The surgical risk has been further reduced by the development of traditional trabeculectomy to modern modified trabeculectomy including application of antimetabolites and use of adjustable sutures, which improves the long-term outcomes. However, since trabeculectomy still can not effectively control the amount of aqueous humor drainage, it is not considered as an ideal operation method. Under these circumstances, non-penetrating glaucoma surgery was brought up again.

Since the non-penetrating glaucoma surgery was introduced to China in the 1990s, a large number of clinical and basic researches have been conducted by domestic experts and scholars. The skills and postoperative managements of the non-penetrating glaucoma surgery have been continuously developed and improved, and there are many reports both home and abroad in this aspect. Canaloplasty is a new anti-glaucoma surgical technique that has emerged in recent years, which is an unfilterable surgery wherein the suture is implanted into Schlemm's canal via a special microcatheter to expand Schlemm's canal and the trabecular meshwork so as to reconstruct a natural outflow channel for aqueous humor, thereby reducing intraocular pressure to treat glaucoma. Surgeries not dependent on filtering bleb have drawn more and more attention from ophthalmologists because there is no formation of conjunctival filtering bleb, avoiding resulting complications such as dryness and discomfort of ocular surface, change in immune structure, easy infection, etc., and its clinical applications have shown that it has a good and safe IOP lowering effect. However, canaloplasty requires special devices and materials, costs a lot, is complicate to operate and has a high requirement for the surgeons, and the current study shows that canaloplasty is only applicable to open-angle glaucoma because angle-closure glaucoma becomes a surgical contraindication due to adhesion and obstruction of iris at the chamber angle, therefore it cannot be clinically used in a wide range.

SUMMARY

In order to overcome the drawbacks of the prior art, the present invention provides a method for preparation of an alternative biomimetic stent for glaucoma internal drainage and a method for using the same.

The technical solution adopted by the present invention is that: an alternative biomimetic stent for glaucoma internal drainage comprises a cylindrical tube body which has a hollow structure provided inside with a plurality of straight tubes that support the tube wall of the tube body.

The number of the straight tubes is three, the straight tubes have a circular cross-section, and the three circular straight tubes are arranged in a triangle within the hollow structure of the tube body.

The number of the straight tubes is four, the straight tubes have a circular cross-section, and the four circular straight tubes are arranged in a quadrangle within the hollow structure of the tube body.

The straight tubes have a polygonal cross-section, and the plurality of polygonal straight tubes are closely arranged on the inner wall of the hollow structure of the tube body.

The tube body has a tube length of 6 mm and a cross-sectional diameter of 300 μm.

The biomimetic stent is made of polyurethane.

A method for using the alternative biomimetic stent for glaucoma internal drainage comprises the following steps: routinely disinfecting a surgical eye, placing blepharostat, rinsing conjunctival sac, taking 0.4 ml of 2% Lidocaine to place into conjunctiva of the surgical eye for local anaesthesia, then making fixation by superior rectus traction suture, according to clock positions, cutting the conjunctiva around the eye along the edge from the 11 o'clock position to the 1 o'clock position, making a superficial scleral flap with a size of 4×4 mm which is ⅓ of the thickness of schlera that uses corneal limbus as fundus with the 12 o'clock position as a center, making a deep scleral flap with a size of 3×3 mm which is about ⅔ of the thickness of the schlera beneath the superficial scleral flap, then peeling in the direction of cornea to find Schlemm's canal and cutting up the outer wall of Schlemm's canal, injecting polymer hyaluronic acid to both ends of Schlemm's canal with a 30G needle so that the biomimetic stent can easily pass through the opening, cutting off the deep scleral flap, and at 1.0 mm in corneal limbus in the 9 o'clock or 3 o'clock position, making paracentesis of anterior chamber parallel to the direction of iris, gently pressing the trailing edge of the puncture incision to discharge aqueous humor and reduce intraocular pressure, implanting two segments of the biomimetic stents into the openings at two ends of Schlemm's canal respectively after the decompression puncture of anterior chamber until the stent is entirely implanted in Schlemm's canal, then taking out 1.0 mm×1.5 mm of deep trabecular tissue between Schlemm's canal and cornea with a scleral punch, and pruning away corresponding iris root tissue, closing and suturing scleral flap, injecting balanced salt solution through the puncture incision of anterior chamber for the purpose of observation, and suturing conjunctival flap after the intraocular pressure returns to the normal level.

The present invention has the following beneficial effects: the present invention provides an alternative biomimetic stent for glaucoma internal drainage and a method for using the same, by suitably placing and fixing the biomimetic stent, aqueous humor can smoothly flow into Schlemm's canal through the tube mouth expanded by the biomimetic stent, so that the collapsed Schlemm's canal can be re-expanded with the aqueous humor infusion, and the purpose of treatment of glaucoma by reducing the intraocular pressure can be achieved by drainage of aqueous humor into a collecting tube and aqueous humor veins. The scarring issue of the tube mouth can be effectively solved by implanting biomimetic stent material that expands the mouth of Schlemm's canal to achieve the effect of long-term reduction of intraocular pressure. Meanwhile, for patients with angle-closure glaucoma, trabeculectomy can be locally combined to solve adhesion and obstruction of iris at the anterior chamber angle, so that aqueous humor flows from the anterior chamber into the broken end of Schlemm's canal via the incision around trabecula of tiris, flows into Schlemm's canal via the mouth of Schlemm's canal expanded by the biomimetic stent, and then flows out via a collecting tube and aqueous humor veins, so as to achieve the purpose of treating glaucoma by reducing the intraocular pressure.

DETAILED DESCRIPTION

Figure 1:
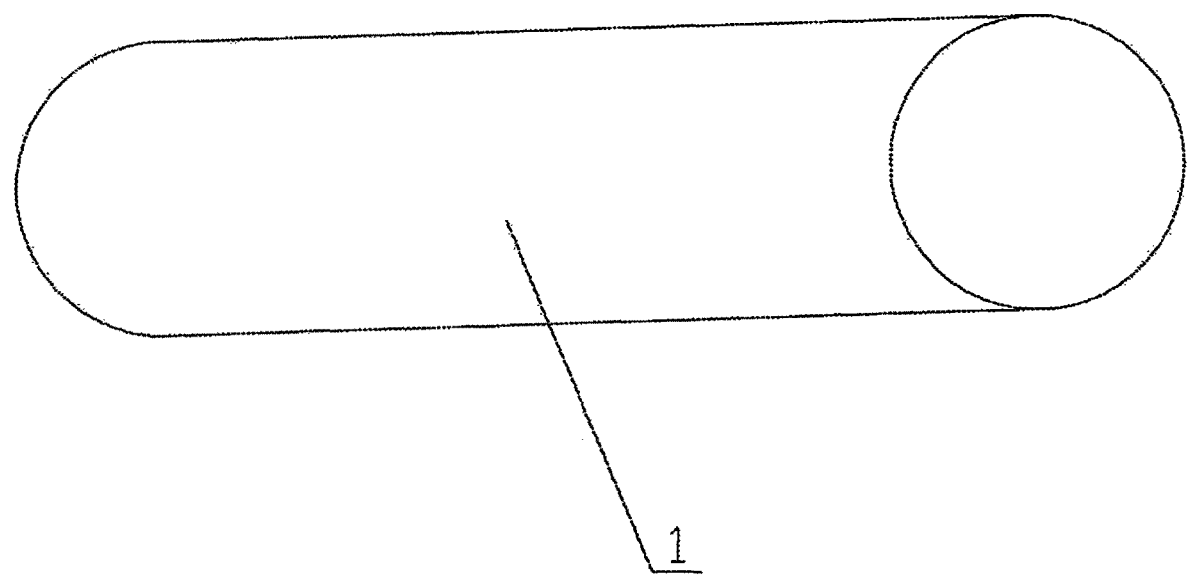
FIG. 1 is a structure diagram of the present invention.
Figure 2:
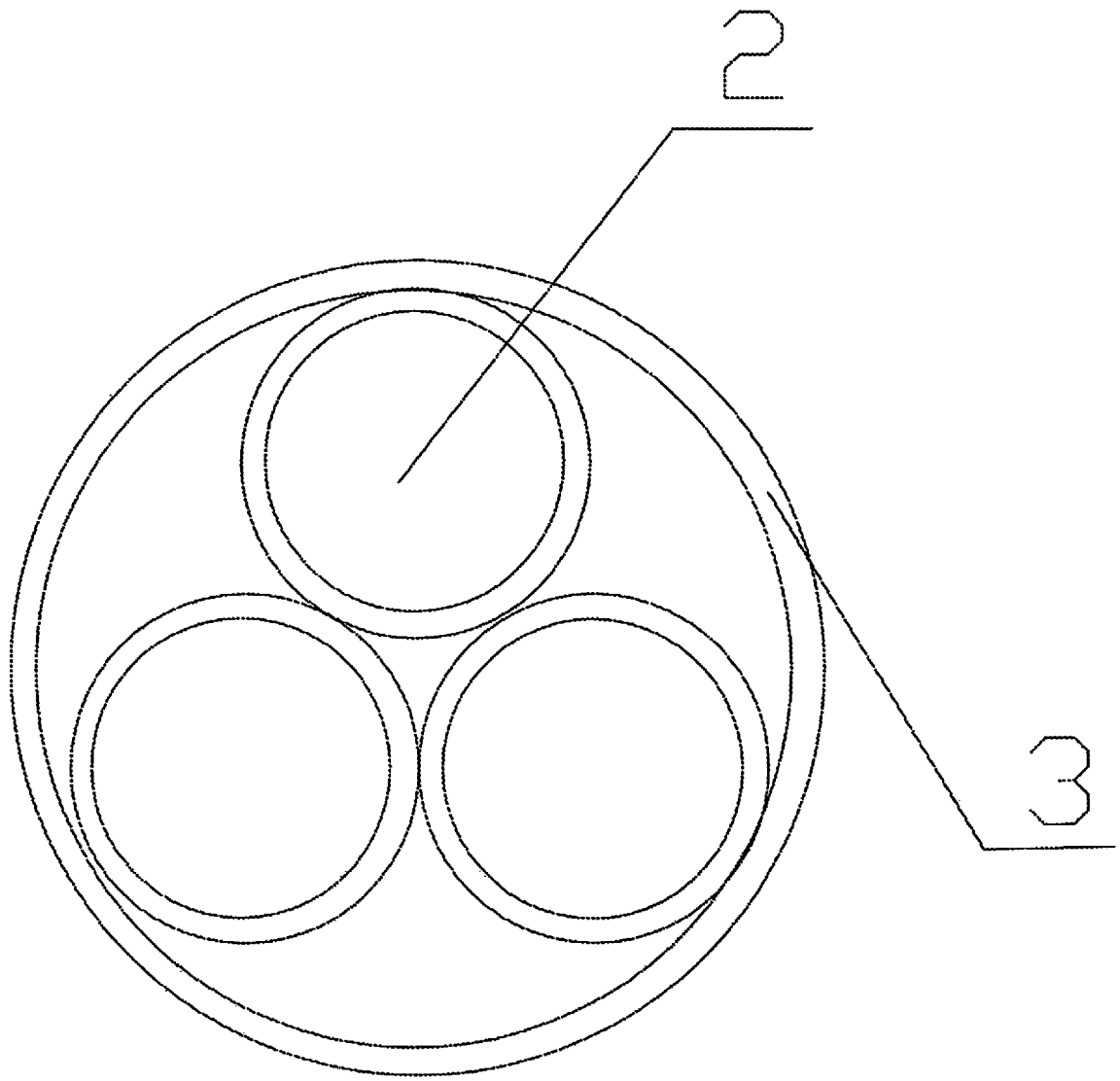
FIG. 2 is a structure diagram of the present invention.
Figure 3:
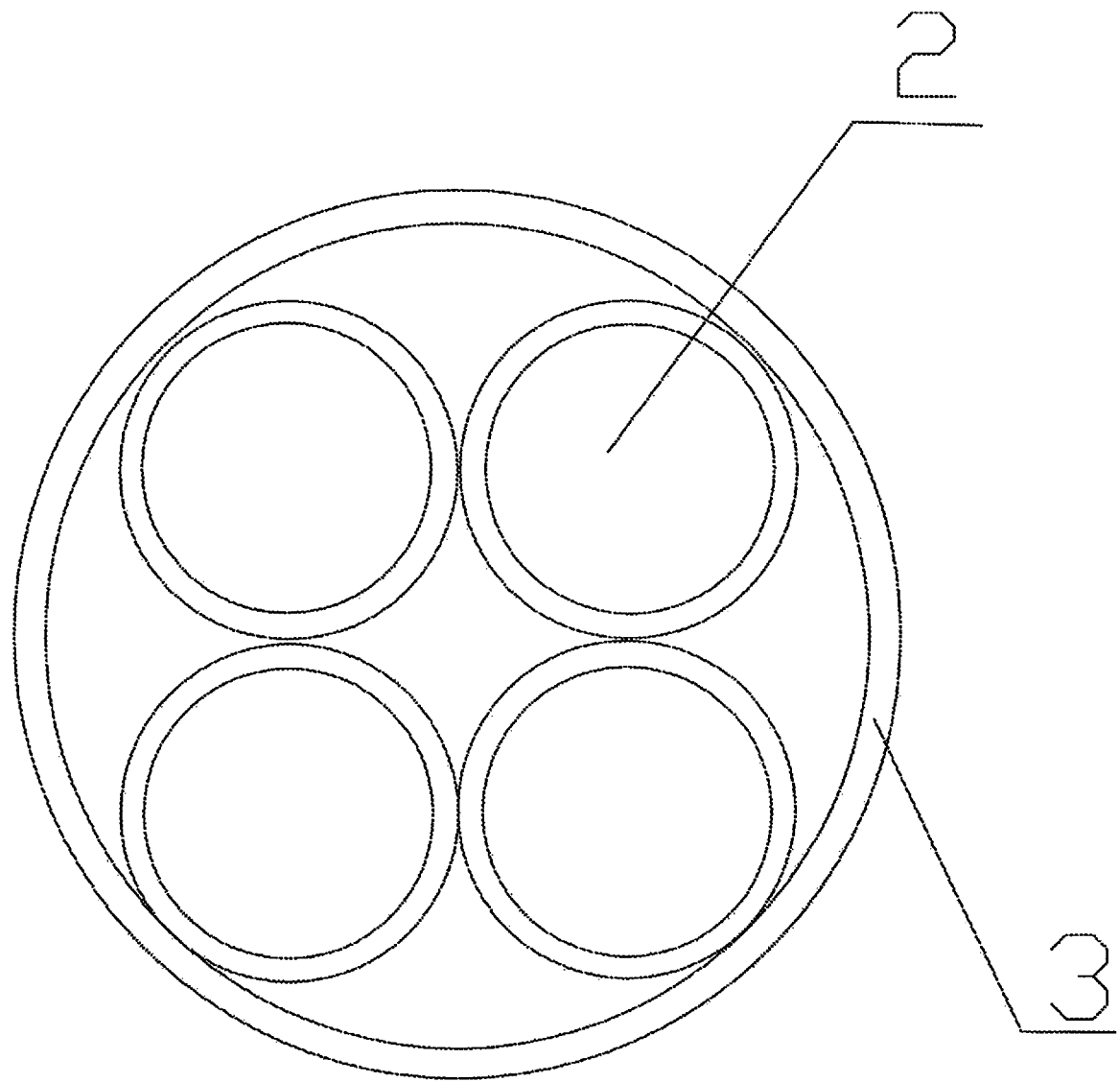
FIG. 3 is a structure diagram of the present invention.
Figure 4:
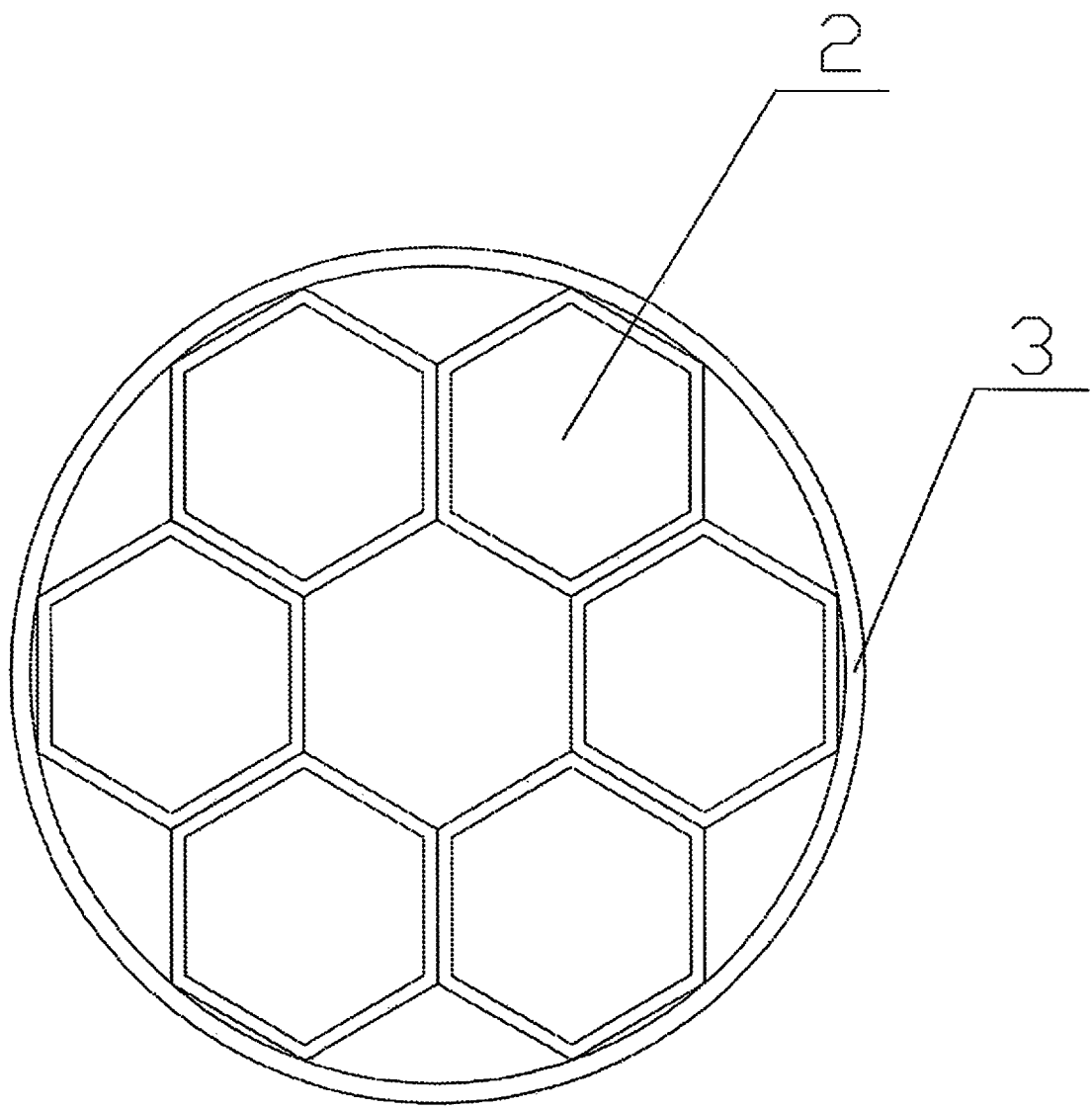
FIG. 4 is a structure diagram of the present invention.
In the drawings, 1—tube body, 2—straight tube, and 3—tube wall.

The present invention will be further described with reference to FIGS. 1~4.

Example 1

An alternative biomimetic stent for glaucoma internal drainage comprises a cylindrical tube body 1 which has a hollow structure provided inside with three straight tubes 2 that support the tube wall 3 of the tube body 1, the straight tubes 2 have a circular cross-section, and the three circular straight tubes 2 are arranged in a triangle within the hollow structure of the tube body 1. The tube body 1 has a tube length of 6~10 mm and a cross-sectional diameter of 300 µm. The biomimetic stent is made of polyurethane.

Example 2

An alternative biomimetic stent for glaucoma internal drainage comprises a cylindrical tube body 1 which has a hollow structure provided inside with four straight tubes 2 that support the tube wall 3 of the tube body 1, the straight tubes 2 have a circular cross-section, and the four circular straight tubes 2 are arranged in a quadrangle within the hollow structure of the tube body 1. The tube body 1 has a tube length of 6 mm and a cross-sectional diameter of 300 µm. The biomimetic stent is made of polyurethane.

Example 3

An alternative biomimetic stent for glaucoma internal drainage comprises a cylindrical tube body 1 which has a hollow structure provided inside with six straight tubes 2 that support the tube wall 3 of the tube body 1, the straight tubes 2 have a polygonal cross-section, and the plurality of polygonal straight tubes 2 are closely arranged on the inner wall of the hollow structure of the tube body 1. The tube body 1 has a tube length of 6 mm and a cross-sectional diameter of 300 µm. The biomimetic stent is made of polyurethane.

The Placement Process of the Biomimetic Stent:

A surgical eye is routinely disinfected and draped, a blepharostat is placed, conjunctival sac is rinsed with diluted iodophor solution, after 0.4 ml of 2% Lidocaine is taken to place into conjunctiva of the surgical eye for local anaesthesia, fixation of superior rectus traction suture is made, according to clock positions, conjunctiva around the eye is cut along the edge from the 11 o'clock position to the 1 o'clock position, superficial scleral flap with a size of 4×4 mm which is ⅓ of the thickness of the schlera is made with corneal limbus as fundus taking the 12 o'clock position as a center, then deep scleral flap with a size of 3×3 mm which is about ⅔ of the thickness of schlera is made beneath the superficial scleral flap. Peeling is carried out in the direction of cornea to find Schlemm's canal and the outer wall of Schlemm's canal is cut up, then polymer hyaluronic acid (Healon GV) is injected to both ends of Schlemm's canal with a 30G needle, so that the biomimetic stent can easily pass through the opening, and the deep scleral flap is cut off. At 1.0 mm in corneal limbus in the 9 o'clock or 3 o'clock direction, paracentesis of anterior chamber parallel to the direction of iris is made, the trailing edge of puncture incision is gently pressed to discharge aqueous humor and reduce intraocular pressure, two segments of biomimetic stent are implanted into the openings at two ends of Schlemm's canal respectively after the decompression puncture of anterior chamber until the stent is entirely implanted in Schlemm's canal. Then 1.0 mm×1.5 mm of deep trabecular tissue between Schlemm's canal and cornea is taken out with a scleral punch, and the corresponding iris root tissue is pruned away, scleral flap is closed and seamed for 4 stitches with 10-0 polypropylene sutures, a balanced salt solution is injected through the puncture incision of anterior chamber for the purpose of observation, and no leakage is taken as watertight suture, conjunctival flap is seamed for 2 stitches with 10-0 polypropylene sutures after the intraocular pressure returns to the normal level. Anti-inflammatory drugs are administrated postoperation, intraocular pressure and the responses of the ocular anterior segment are monitored, a single eye is pressured and bound up postoperation.

The biomimetic stent of the present invention is made of polyurethane material. Regarding the material safety, the research team prepared artificial blood vessels with polyurethane material in the early stage, and after six months of animal experiments, it is observed that this material does not produce any inflammatory response, proving that the material has good application safety. The biomimetic stent is of a hollow porous design, which allows aqueous humor to pass through, and the pores can ensure sufficient flexibility of the material so that it can expand the Schlemm's canal wall and maintain the aqueous humor drainage function for a long period of time without deformation.

The foregoing descriptions are merely preferred embodiments of the present invention, and the protection scope of the present invention is not limited thereto. All the technical solutions under the conception of the present invention fall within the protection scope of the present invention. It should be noted that several improvements and modifications may be made by an ordinary person skilled in the art without departing from the principles of the present invention, and that such improvements and modifications should also be regarded as within the protection scope of the present invention.

The invention claimed is:

1. A method for using an alternative biomimetic stent for glaucoma internal drainage, comprising the following steps: disinfecting a surgical eye, placing a blepharostat, rinsing a conjunctival sac of the surgical eye, placing 0.4 ml of 2% Lidocaine into conjunctiva of the surgical eye for local anesthesia, then making fixation by superior rectus traction suture, according to clock positions, cutting the conjunctiva around the surgical eye along an edge of the surgical eye from an 11 o'clock position to a 1 o'clock position, making a superficial scleral flap with a size of 4×4 mm which is ⅓ of a thickness of sclera that uses corneal limbus as fundus with a 12 o'clock position as a center, making a deep sclera flap with a size of 3×3 mm which is about ⅔ of the thickness of sclera beneath the superficial scleral flap, then peeling back the deep sclera flap in a direction of a cornea of the surgical eye to find Schlemm's canal and cutting an outer wall of Schlemm's canal of the surgical eye to make opening ends, injecting polymer hyaluronic acid to both opening ends of Schlemm's canal with a 30 G needle so that the biomimetic stent is capable to pass through the openings, cutting off the deep scleral flap, and at 1.0 mm in corneal limbus in a 9 o'clock or 3 o'clock position, making paracentesis of an anterior chamber of the surgical eye parallel to a direction of an iris of the surgical eye, pressing a trailing edge of a puncture incision formed from the paracentesis to discharge aqueous humor to reduce intraocular pressure, implanting two biomimetic stents into the openings at two opening ends of Schlemm's canal respectively after a decompression puncture of the anterior chamber until the biomimetic stent is entirely implanted in Schlemm's canal, then taking out 1.0 mm×1.5 mm of deep trabecular tissue between Schlemm's canal and the cornea with a scleral punch, and pruning away corresponding iris root tissue, closing and suturing the superficial scleral flap, injecting salt solution through the puncture incision of the anterior chamber for observation, and suturing a conjunctival flap after the intraocular pressure is reduced.

2. The method for using the alternative biomimetic stent for glaucoma internal drainage according to claim 1, wherein the alternative biomimetic stent comprising a cylindrical tube body with a hollow structure, a plurality of straight tubes, provided in the cylindrical tube body to support a tube wall of the cylindrical tube body.

3. The method for using the alternative biomimetic stent for glaucoma internal drainage according to claim 2, wherein a number of the plurality of straight tubes is three, each of the plurality of straight tubes has a circular cross-section, and the three circular straight tubes are arranged in a triangle within the hollow structure of the cylindrical tube body.

4. The method for using the alternative biomimetic stent for glaucoma internal drainage according to claim 2, wherein a number of the plurality of straight tubes is four, each of the plurality of straight tubes has a circular cross-section, and the four circular straight tubes are arranged in a quadrangle within the hollow structure of the cylindrical tube body.

5. the method for using the alternative biomimetic stent for glaucoma internal drainage according to claim 1, wherein the straight tubes have a polygonal cross-section, and the plurality of polygonal straight tubes are closely arranged on an inner wall of the hollow structure of the cylindrical tube body.

6. The method for using the alternative biomimetic stent for glaucoma internal drainage according to claim 5, wherein each cylindrical tube body has a tube length of 6 mm and a cross-sectional diameter of 300 μm.

7. the method for using the alternative biomimetic stent for glaucoma internal drainage according to claim 6, wherein the biomimetic stent is made of polyurethane.

8. A method for using an alternative biomimetic stent for glaucoma internal drainage, comprising the following steps: disinfecting a surgical eye, placing a blepharostat, rinsing a conjunctival sac of the surgical eye, placing 0.4 ml of 2% Lidocaine into conjunctiva of the surgical eye for local anesthesia, then making fixation by superior rectus traction suture, according to clock positions, cutting the conjunctiva around the surgical eye along an edge of the surgical eye from an 11 o'clock position to a 1 o'clock position, making a superficial scleral flap with a size of 4×4 mm which is ⅓ of a thickness of sclera that uses corneal limbus as fundus with a 12 o'clock position as a center, making a deep sclera flap with a size of 3×3 mm which is about ⅔ of the thickness of sclera beneath the superficial scleral flap, then peeling back the deep sclera flap in a direction of a cornea of the surgical eye to find Schlemm's canal and cutting an outer wall of Schlemm's canal of the surgical eye to make opening ends, injecting polymer hyaluronic acid to both opening ends of Schlemm's canal with a 30 G needle so that the biomimetic stent is capable to pass through the openings, cutting off the deep scleral flap, and at 1.0 mm in corneal limbus in a 9 o'clock or 3 o'clock position, making paracentesis of an anterior chamber of the surgical eye parallel to a direction of an iris of the surgical eye, pressing a trailing edge of a puncture incision formed from the paracentesis to discharge aqueous humor to reduce intraocular pressure, implanting two biomimetic stents into the openings at two opening ends of Schlemm's canal respectively after a decompression puncture of the anterior chamber until the biomimetic stent is entirely implanted in Schlemm's canal, then taking out 1.0 mm×1.5 mm of deep trabecular tissue between Schlemm's canal and the cornea with a scleral punch, and pruning away corresponding iris root tissue, closing and suturing the superficial scleral flap, injecting salt solution through the puncture incision of the anterior chamber for observation, and suturing a conjunctival flap after the intraocular pressure is reduced; wherein the alternative biomimetic stent comprises a cylindrical tube body with a hollow structure, a plurality of straight tubes, provided in the cylindrical tube body to support a tube wall of the cylindrical tube body, and wherein two alternative biomimetic stents are configured to be respectively implanted into two broken opening ends of Schlemm's canal of an eye formed by cutting off a part of Schlemm's canal to keep the two broken opening ends expanding.

9. The method for using the alternative biomimetic stent for glaucoma internal drainage according to claim 8, wherein a number of the plurality of straight tubes is three, each of the plurality of straight tubes has a circular cross-section, and the three circular straight tubes are arranged in a triangle within the hollow structure of the cylindrical tube body.

10. The method for using the alternative biomimetic stent for glaucoma internal drainage according to claim 8, wherein a number of the plurality of straight tubes is four, each of the plurality of straight tubes has a circular cross-section, and the four circular straight tubes are arranged in a quadrangle within the hollow structure of the cylindrical tube body.

11. the method for using the alternative biomimetic stent for glaucoma internal drainage according to claim 8, wherein the straight tubes have a polygonal cross-section, and the plurality of polygonal straight tubes are closely arranged on an inner wall of the hollow structure of the cylindrical tube body.

12. The method for using the alternative biomimetic stent for glaucoma internal drainage according to claim 11, wherein each cylindrical tube body has a tube length of 6 mm and a cross- sectional diameter of 300 µm.

13. the method for using the alternative biomimetic stent for glaucoma internal drainage according to claim 12, wherein the biomimetic stent is made of polyurethane.

* * * * *